(12) United States Patent
Vitense et al.

(10) Patent No.: US 8,948,868 B2
(45) Date of Patent: Feb. 3, 2015

(54) METHODS AND APPARATUS FOR MANUALLY SUSPENDING INTRATHORACIC IMPEDANCE FLUID STATUS MEASUREMENTS

(75) Inventors: Holly S. Vitense, Maple Grove, MN (US); Li Wang, Hong Kong (CN); Denise Dirnberger, Blaine, MN (US); Melissa M. Rhodes, Columbia Heights, MN (US); Douglas A. Hettrick, Andover, MN (US); Shantanu Sarkar, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 2296 days.

(21) Appl. No.: 11/554,825

(22) Filed: Oct. 31, 2006

(65) Prior Publication Data
US 2008/0103530 A1 May 1, 2008

(51) Int. Cl.
| | | |
|---|---|---|
| *A61N 1/00* | (2006.01) | |
| *A61N 1/372* | (2006.01) | |
| *A61B 5/00* | (2006.01) | |
| *A61B 5/0215* | (2006.01) | |
| *A61B 5/053* | (2006.01) | |

(52) U.S. Cl.
CPC ............ *A61N 1/37258* (2013.01); *A61B 5/0031* (2013.01); *A61B 5/0215* (2013.01); *A61B 5/053* (2013.01); *A61N 1/37247* (2013.01)
USPC ....................... 607/28; 607/9; 607/17; 607/27

(58) Field of Classification Search
USPC .............. 607/9, 14, 17, 18, 23, 27, 30, 32, 28
See application file for complete search history.

(56) References Cited

U.S. PATENT DOCUMENTS

| | | | |
|---|---|---|---|
| 3,780,727 A * | 12/1973 | King .............................. | 600/510 |
| 4,140,131 A | 2/1979 | Dutcher et al. | |
| 4,223,801 A * | 9/1980 | Carlson ............................ | 221/3 |
| 4,823,797 A | 4/1989 | Heinze et al. | |
| 5,076,272 A * | 12/1991 | Ferek-Petric ................... | 607/28 |
| 5,200,891 A * | 4/1993 | Kehr et al. ........................ | 221/2 |
| 5,313,953 A | 5/1994 | Yomtov et al. | |
| 5,411,031 A | 5/1995 | Yomtov | |

(Continued)

FOREIGN PATENT DOCUMENTS

| | | |
|---|---|---|
| WO | WO9833553 A1 | 8/1998 |
| WO | WO9838909 A | 9/1998 |

(Continued)

*Primary Examiner* — Niketa Patel
*Assistant Examiner* — William Levicky
(74) *Attorney, Agent, or Firm* — Carol F. Barry

(57) ABSTRACT

The capability to suspend a patient alert relating to a monitored physiologic parameters addresses a need to selectively shut off a patient-alert signal or signals during the time a patient is being treated for an excursion in the parameter. Of course, in general a signal call attention to a patient's a potentially deleterious status or condition for which they should seek medical attention. Once a chronically-implanted monitoring device has detected or provided information about the parameter relative to a desired value, trend, or range and a clinician has been notified and intervened the alert signal is temporarily disabled for a predetermined period. That is, once the notification occurs and alert has served its purpose, the alert mechanism is selectively deactivated while the patient ostensibly begins to gradually correct the monitored physiologic parameter under a caregiver's direction and control. After which time, the alert will reactivate.

6 Claims, 4 Drawing Sheets

(56) References Cited

U.S. PATENT DOCUMENTS

| | | | |
|---|---|---|---|
| 5,642,731 A * | 7/1997 | Kehr | 600/300 |
| 5,720,771 A * | 2/1998 | Snell | 607/60 |
| 5,732,693 A * | 3/1998 | Bathe et al. | 128/203.12 |
| 5,836,975 A | 11/1998 | DeGroot | |
| 5,876,353 A | 3/1999 | Riff | |
| 5,891,180 A * | 4/1999 | Greeninger et al. | 607/32 |
| 5,897,577 A | 4/1999 | Cinbis et al. | |
| 6,154,674 A | 11/2000 | Meier | |
| 6,216,038 B1 * | 4/2001 | Hartlaub et al. | 607/31 |
| 6,263,243 B1 | 7/2001 | Lang | |
| 6,386,882 B1 * | 5/2002 | Linberg | 434/262 |
| 6,405,085 B1 | 6/2002 | Graupner et al. | |
| 6,409,675 B1 * | 6/2002 | Turcott | 600/508 |
| 6,463,326 B1 | 10/2002 | Hartley et al. | |
| 6,546,288 B1 | 4/2003 | Levine | |
| 6,721,600 B2 | 4/2004 | Jorgenson et al. | |
| 6,804,558 B2 * | 10/2004 | Haller et al. | 607/30 |
| 7,065,409 B2 * | 6/2006 | Mazar | 607/60 |
| 7,089,057 B2 * | 8/2006 | Heathershaw et al. | 607/27 |
| 7,117,035 B2 * | 10/2006 | Wagner et al. | 607/17 |
| 7,149,773 B2 * | 12/2006 | Haller et al. | 709/203 |
| 7,184,821 B2 * | 2/2007 | Belalcazar et al. | 600/547 |
| 7,526,345 B2 | 4/2009 | Covey et al. | |
| 2001/0051787 A1 * | 12/2001 | Haller et al. | 604/66 |
| 2003/0028223 A1 * | 2/2003 | Olson | 607/27 |
| 2004/0172080 A1 * | 9/2004 | Stadler et al. | 607/17 |
| 2004/0199212 A1 * | 10/2004 | Fischell et al. | 607/32 |
| 2004/0220633 A1 * | 11/2004 | Wagner et al. | 607/9 |
| 2005/0124900 A1 | 6/2005 | Stadler et al. | |
| 2005/0137480 A1 * | 6/2005 | Alt et al. | 600/508 |
| 2005/0216067 A1 * | 9/2005 | Min et al. | 607/17 |
| 2006/0149324 A1 * | 7/2006 | Mann et al. | 607/9 |
| 2006/0258952 A1 | 11/2006 | Stahmann et al. | |
| 2007/0156059 A1 * | 7/2007 | Vitali et al. | 600/529 |
| 2007/0191901 A1 * | 8/2007 | Schecter | 607/17 |
| 2008/0024293 A1 | 1/2008 | Stylos | |
| 2009/0018597 A1 * | 1/2009 | Wenzel et al. | 607/23 |

FOREIGN PATENT DOCUMENTS

| | | | | |
|---|---|---|---|---|
| WO | WO 9838909 A1 * | 9/1998 | | A61B 5/021 |
| WO | WO2004050178 A1 | 6/2004 | | |
| WO | WO2005065538 A | 7/2005 | | |
| WO | WO2006127719 A2 | 11/2006 | | |

* cited by examiner

METHODS AND APPARATUS FOR MANUALLY SUSPENDING INTRATHORACIC IMPEDANCE FLUID STATUS MEASUREMENTS

FIELD OF THE INVENTION

The present invention relates to improved methods and apparatus for monitoring the intra-thoracic fluid status of an individual and selectively permitting a reduction in notification(s) regarding the status during times when the status is being acutely adjusted.

This patent disclosure hereby incorporates the entire contents of non-provisional U.S. patent application Ser. No. 10/727,008 filed 3 Dec. 2003 and entitled, "Method and Apparatus for Detecting Change in Intrathoracic Electrical Impedance", patent application, allowed Mar. 28, 2010 and U.S. Pat. No. 6,599,250 issued 29 Jul. 2003 to Webb and Bennett and entitled, "Heart Failure Monitor Quicklook Summary for Patient Management Systems."

SUMMARY

The capability to suspend a patient alert comes addresses a need to selectively shut off a signal related to an undesirable trend, range, or value of a physiologic parameter of a patient. For instance, an audible patient-alert tone can be disabled during the time a patient is being treated for an excursion in the parameter (e.g., intra-thoracic fluid accumulation). Of course, in general an alert signaling regime notifies a patient, caregiver, and/or clinician attention of a potentially deleterious heart failure event such as an acute decompensation for which they should seek medical attention. In one embodiment, a chronically-implanted intra-thoracic fluid status monitoring device is interrogated by an external programming device and the patient evaluated and a caregiver then can optionally suspend the alert notification process for a predetermined period. Thus, according to the invention once the patient notification or alert has occurred, the alert mechanism is selectively deactivated while the patient ostensibly begins to gradually correct the excursion under a physician's direction and control. After a predetermined period of time the alert will reactivate.

The inventive user interface (UI) screens described herein, and their functionality, are designed to meet many of the following user requirements: clinicians must not be forced to schedule a special office visit to just turn on or off the alert and patients then do not need to be subjected to undesired, frequent (e.g., daily) alert tones.

Ultimately, suspension of the alert must be implemented in a way to preserve the feature's ability to detect a subsequent excursion in the patient's fluid status (trend or acute readings). Implementing alert suspension is designed so that it will not affect the storage or graphing of the fluid status and/or fluid status trend. The alert is thus suspended by programming a "suspend" parameter (e.g., via a programmable-field window launched from an external programmer for an implantable medical device). In one form of the invention, a parameter-launched selection menu with a response (i.e., yes/no) and a series of days (e.g., 2, 3, 5, 7, 9, 12, 14 days) selections. If a number of day selection is made, below the value selection field, a text message will show when the fluid status monitoring alert will resume (e.g., "resume alert on 30-January-05").

In addition, optionally a feedback loop acknowledges that the alert was suspended by a notation added to the patient's report and/or the trends on a long-term tracking report. A similar notation can also appear in an events log so users can track the operation of the intra-thoracic fluid status. To maintain consistency, it is proposed that when an audible alert is suspended, a related, complementary wireless transmission of same can also be suspended.

DETAILED DESCRIPTION OF THE ILLUSTRATED EMBODIMENTS

In the following detailed description, references are made to illustrative embodiments for improved physiologic monitoring of potentially deleterious and/or pathogenic patient conditions wherein following clinical intervention notification signaling schemes are temporarily suspended.

The present invention provides enhanced intra-thoracic impedance measurements for the detection of hemodynamic changes, in particular fluid retention. Three components of intra-thoracic impedance are used to determine fluid overload; namely, 1) daily thoracic impedance measurements, 2) thoracic reference impedance, and 3) fluid index threshold. When the daily thoracic impedance and reference impedance diverge the fluid index increases. Once the fluid index passes the user programmable threshold, if enabled, an audible alert sounds from the implantable device. The audible alert will sound daily as long as the fluid index is greater than the threshold. The capability to suspend the alert was designed to address the situation whereby a patient and/or clinician simply needs silence from the device alerts during, for example a recovery period or when under acute observation in a clinical setting. As it is currently designed, when enabled, the intra-thoracic impedance algorithm triggers an audible device alert when, for instance, a heart failure decomposition event is detected. After the patient has been seen, evaluated, and properly treated by a clinician, ideally the daily impedance should recover (i.e., increase) and rejoin the reference impedance. Because the speed at which the patient's daily impedance measurements change is typically more rapid than the response of the thoracic impedance reference, the alert can continue being activated for an extended period (e.g., on a daily basis for several days) during a recovery period.

Figure 1:
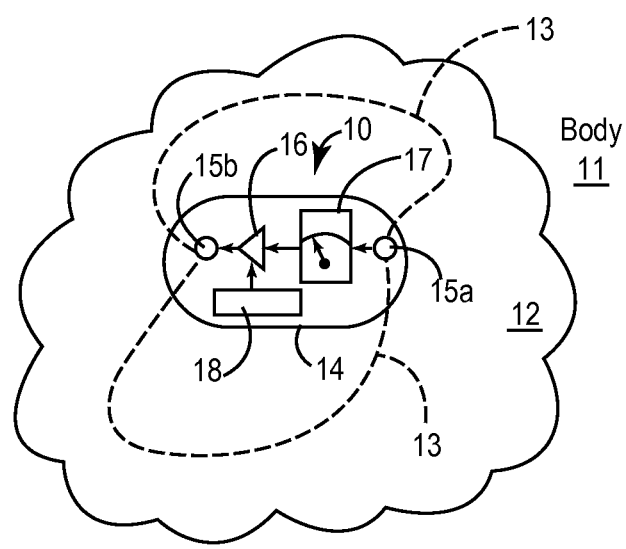
FIG. 1 illustrates in a schematic form an implantable medical device according to an embodiment of the present invention.

FIG. 1 is a schematic diagram of an implantable medical device according to an embodiment of the present invention. In the heuristic drawing of FIG. 1, a section of a body 11 is shown with a cut-away area 12 to allow for illustration of an implantable medical device according to an embodiment of the present invention. As illustrated in FIG. 1, an exemplary embodiment of an implantable medical device 10 includes two electrodes 15a and 15b on the surface of a shell 14 of device 10. Power is provided to the circuitry internal to the shell 14 by a power supply 18, which drives a stimulation circuit 16, sending electrons through various pathways in the body (such pathways are heuristically illustrated as being primarily in the area surrounded by dotted line 13) between electrodes 15a and 15b. An impedance measurement device 17 determines the impedance of the circuit pathway 13.

According to an embodiment of the present invention, because of the possible poor signal characteristics that may be found using the same electrodes for generating the impedance test pulse signal and taking the measurement from the same electrodes, impedance measurements are made in a uniform part (or relatively noiseless area) of the field. One way to do this is using one electrode, electrically isolated from the large surface indifferent electrode (like the can or housing of a pacemaker, device 10, or other implant) to deliver the test pulse, and a second electrically isolated electrode to measure the voltage difference in the tissue between the indifferent electrode and this second electrode. Another embodiment can use two completely independent electrodes in the field to measure the impedance, thus having a quadric-polar system. In various configurations of this invention additional electrodes can be imagined for flexibility where needed or to use electrodes on leads locatable in specific places within the field created by the test, or excite pulse.

Figure 2:
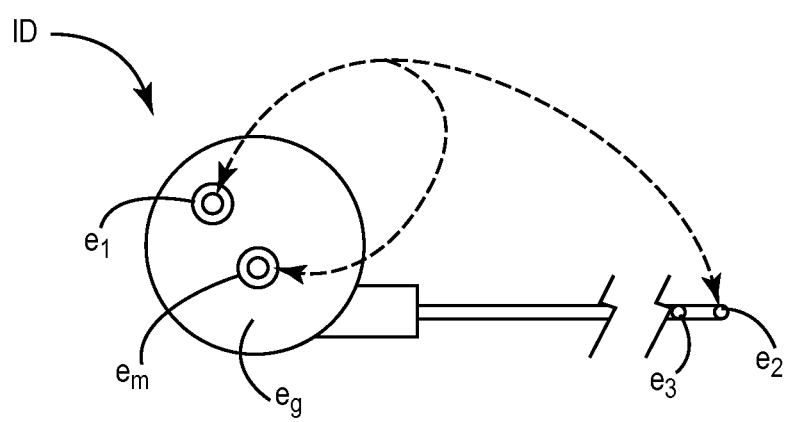
FIG. 2 depicts a schematic diagram of several exemplary electrode configurations in an implantable medical device according to an embodiment of the present invention.

FIG. 2 is a schematic diagram of exemplary electrode configurations in an implantable medical device according to an embodiment of the present invention. This acceptable variety of configuration to achieve different impedance measurement signal values is illustrated, for example, in FIG. 2 wherein an implantable medical device has electrodes denoted e1, e2, eg and em and either electrodes e1 or e2 can be used for developing the test pulses. The value being measured (voltage or impedance of the tissue between these electrode pairs) is taken between another electrically isolated measuring electrode em and the indifferent or ground electrode eg; between em and e1; or between em and e2. Or, of course, the measurement could be taken between the two test pulse delivery electrodes e1, and eg; or between e2 and eg in another embodiment.

As will be described with reference to various figures below, substantial variation can be used for each of the elements described with reference to FIGS. 1-3, and still be within the scope of this invention. For example, according to an embodiment of the present invention, the excitation pulse is delivered between electrodes e3 and eg and the value measured is taken between electrodes e2 and eg. In a exemplary quadrapolar arrangement, the excitation pulse is delivered between electrodes em and e3 and the value measured is taken between electrodes e1 and e2.

Figure 3:
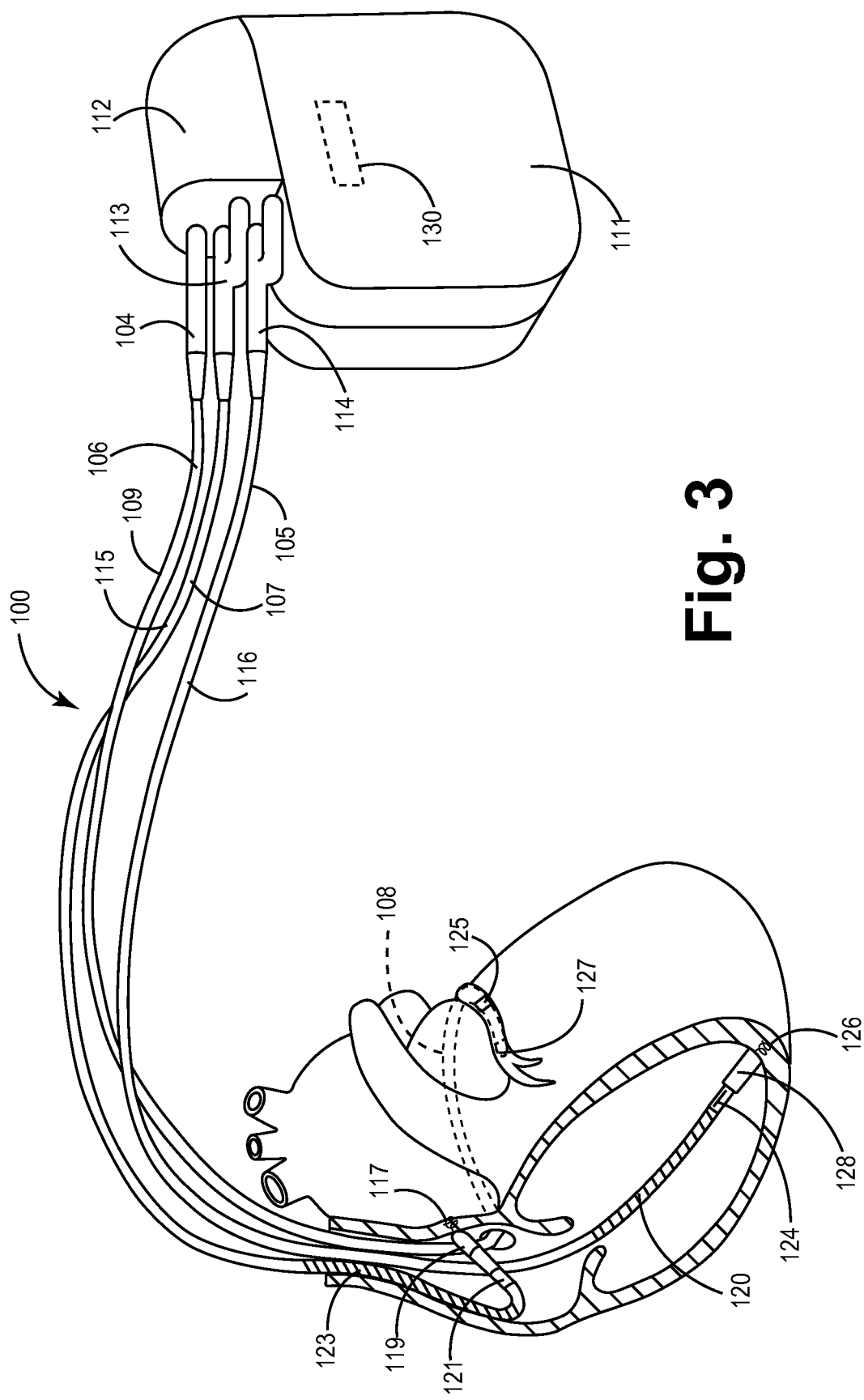
FIG. 3 is a schematic diagram of an implantable medical device in which the present invention may usefully be practiced according to an embodiment of the present invention.

FIG. 3 is a schematic diagram of an implantable medical device in which the present invention may usefully be practiced according to an embodiment of the present invention. As illustrated in FIG. 3, an implantable medical device 100 according to an embodiment of the present invention includes a ventricular lead 105 having an elongated insulative lead body 116 carrying three mutually insulated conductors. Located adjacent the distal end of the lead 105 are a ring electrode 124, an extendable helix electrode 126, mounted retractably within an insulative electrode head 128, and an elongated coil electrode 120. Each of the electrodes 120, 124 and 126 is coupled to one of the three conductors within the lead body 116. Electrodes 124 and 126 are employed for cardiac pacing and for sensing ventricular depolarizations, and electrode 120 is employed for cardioversion and/or defibrillation and for sensing depolarizations, as described below. At the proximal end of the lead 105 is a bifurcated connector 114, which carries three electrical connectors, each coupled to one of the coiled conductors.

An atrial/SVC lead 107 includes an elongated insulative lead body 115, also carrying three mutually insulated conductors. Located adjacent the J-shaped distal end of the lead 107 are a ring electrode 121 and an extendible helix electrode 117, mounted retractably within an insulative electrode head 119. Each of the electrodes 117 and 121 is coupled to one of the conductors within the lead body 115. Electrodes 117 and 121 are employed for atrial pacing and for sensing atrial depolarizations. An elongated coil electrode 123 is provided, proximal to electrode 121 and coupled to the third conductor within the lead body 115. At the proximal end of the lead 107 is a bifurcated connector 113, which carries three electrical connectors, each coupled to one of the coiled conductors.

Any other known lead configurations may also be utilized other the lead configuration of FIG. 3. For example, coil electrode 123 could be located on ventricular lead 105 and positioned within the atrium or SVC by ventricular lead 105 rather than by atrial lead 107.

A coronary sinus/coronary vein lead 109 includes an elongated insulative lead body 106, carrying three conductors, one of which is coupled to an elongated coiled defibrillation electrode 108. Electrode 108, illustrated in broken outline, is located within the coronary sinus and great vein of the heart. Located adjacent the distal end of lead 109 is a ring electrode 125 and a tip electrode 127. Each of electrodes 125-127 is coupled to one of the remaining two of the three conductors located within lead body 106. At the proximal end of the lead 109 is a connector plug 104 that carries an electrical connector, coupled to the coiled conductors.

The implantable medical device 100 includes a hermetically sealed enclosure 111 containing the electronic circuitry (FIG. 4) used for generating cardiac pacing pulses for delivering cardioversion and defibrillation shocks and for monitoring the patient's heart rhythm. Implantable medical device 110 is shown with the lead connector assemblies 104, 113 and 114 inserted into the connector block 112, which serves as a receptacle and electrical connector for receiving the connectors 104, 113 and 114 and interconnecting the leads to the circuitry within enclosure 111.

Insulation of the outward facing portion of the housing 111 of the implantable medical device 110 may be provided or a portion 130 of the outward facing portion may instead be left uninsulated, or some other division between insulated and uninsulated portions may be employed. The uninsulated portion 130 of the housing 111 optionally serves as a subcutaneous defibrillation electrode, used to defibrillate either the atria or ventricles, and as a sensing electrode for sensing depolarizations of the heart. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 4:
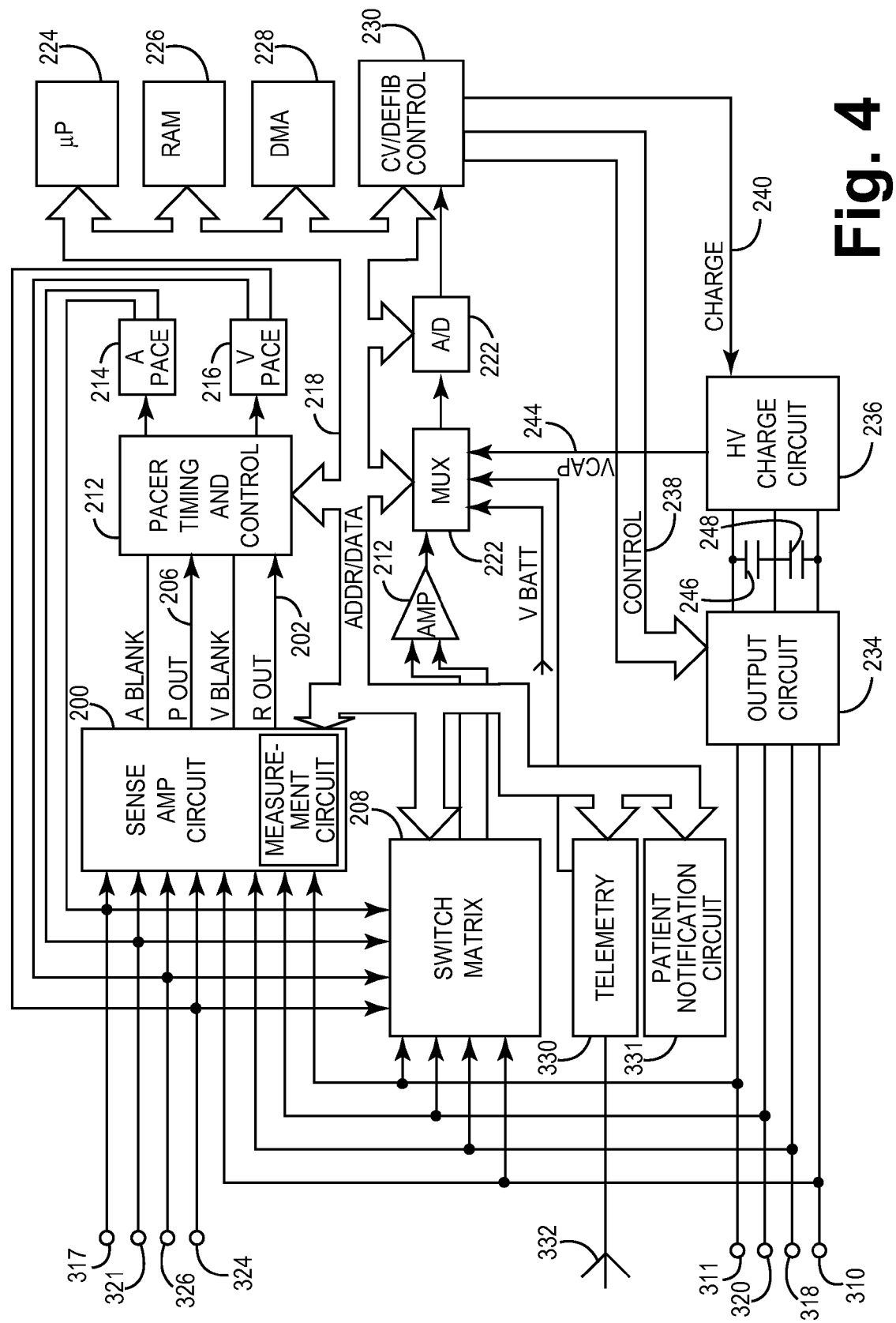
FIG. 4 is a functional block diagram of an exemplary implantable medical device of the type illustrated in FIG. 3, in which the present invention may usefully be practiced.

FIG. 4 is a functional block diagram of an exemplary implantable medical device of the type illustrated in FIG. 3, in which the present invention may usefully be practiced. The device is provided with a lead system including electrodes, which may be as illustrated in FIG. 3. Alternate lead systems may of course be substituted such as pericardial, epicardial, subcutaneous arrays, pairs and single electrodes as is well understood by those of skill in the art. If the electrode configuration of FIG. 3 is employed, the correspondence to the illustrated electrodes is as follows. Electrode 311 corresponds to an electrode formed along the uninsulated portion 130 of the housing of the implantable medical device 110. Electrode 320 corresponds to electrode 120 and is a defibrillation electrode located in the right ventricle. Electrode 310 corresponds to electrode 108 and is a defibrillation electrode located in the coronary sinus. Electrode 318 corresponds to electrode 123 and is a defibrillation electrode located in the superior vena cava. Electrodes 324 and 326 correspond to electrodes 124 and 126, and are used for sensing and pacing in the ventricle. Electrodes 317 and 321 correspond to electrodes 117 and 121 and are used for pacing and sensing in the atrium.

Electrodes 310, 311, 318 and 320 are coupled to high voltage output circuit 234. Electrodes 324 and 326 are coupled to an R-wave amplifier, which preferably takes the form of an automatic gain controlled amplifier providing an adjustable sensing threshold as a function of the measured R-wave amplitude, included in a sense amplifier circuit 200. A signal is generated on R-out line 202 whenever the signal sensed between electrodes 324 and 326 exceeds the present sensing threshold.

Electrodes 317 and 321 are coupled to a P-wave amplifier, which preferably also takes the form of an automatic gain controlled amplifier providing an adjustable sensing threshold as a function of the measured P-wave amplitude, included in sense amplifier circuit 200. A signal is generated on P-out line 206 whenever the signal sensed between electrodes 317 and 321 exceeds the present sensing threshold. Numerous prior art sense amplifiers employed in implantable cardiac pacemakers, defibrillators and monitors may be usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits of sense amplifier circuit 200 produce atrial and ventricular EGM signals which also may be digitized and uplink telemetered to an associated programmer on receipt of a suitable interrogation command. The device may also be capable of generating so-called marker codes indicative of different cardiac events that it detects. The particular telemetry system employed is not critical to practicing the invention, and any of the numerous types of telemetry systems known for use in implantable devices may be used. In particular, the prior telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

A patient notification circuit 331 enables the patient to be notified in the event that it is determined that a significant change in impedance has occurred, as will be in detail described below.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, WI, DVI, VDD, AAI, DDI, DDDR, WIR, DVIR, VDDR, MIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

Arrhythmia detection may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

A measurement circuit 203, similar to measurement circuit 37 and excitation circuit 34 described above in reference to FIG. 4, is utilized in the delivery of excitation pulses and to measure the resulting impedances between a vector formed by any pair of electrodes selected from among electrodes 310, 311, 317, 318, 320, 321, 324 and 326 through connections made in switch matrix 208. Measurement circuit 203, which is coupled to data/address bus 218, can be separate from or may be included within sense amplification circuit 200, as shown.

According to the present invention, once impedance measurement is initiated by microprocessor 224, an excitation pulse is generated by output circuit 234 and applied across an excitation path corresponding to a vector formed by selected electrodes, described above. The excitation pulse may be in the form of either a current pulse or a voltage pulse, and, in either case, may consist of one or more phases of differing polarity, or may correspond to a monophasic, constant voltage pulse for simplicity of implementation. In an embodiment of the present invention, for example, the excitation pulse has an amplitude of approximately 1 volt and a pulse width of approximately 90 microseconds, although any desired amplitude and pulse width may be utilized.

Measurement circuit 203 measures the voltage appearing across a measurement path corresponding to selected measurement electrodes, with the timing of the measurement by measurement circuit 203 being time by timing and control circuit 212 so as to be synchronized with delivery of the excitation pulse. Using the current delivered across the excitation path and the voltage measured across the measure path, microprocessor 224 then calculates the apparent intra-thoracic impedance using Ohm's Law. The process is repeated, so that multiple excitation pulses are delivered over a multiple number of days to generate multiple impedance measurements.

Figure 5:
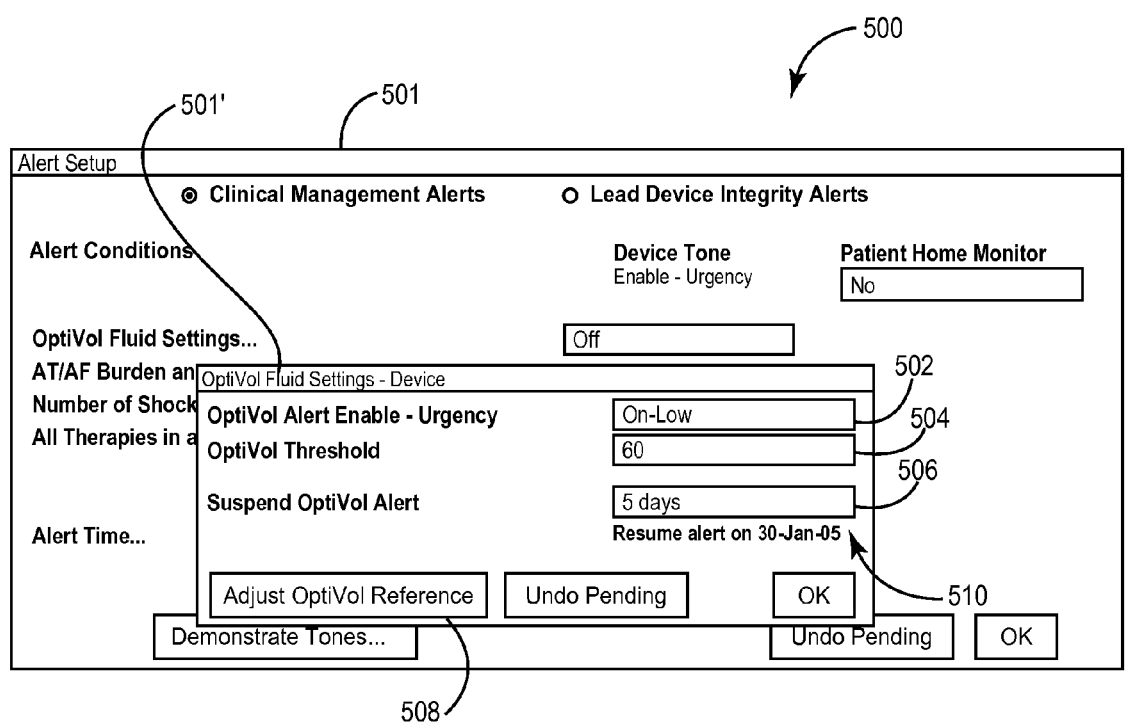
FIG. 5 depicts a graphical user interface having an overlay menu in an embodiment of the invention relating to the OptiVol® fluid status trend feature of Medtronic, Inc.

FIG. 5 depicts a graphical user interface (GUI) 500 having an overlay menu 501, 501' in an embodiment of the invention relating to the OptiVol® intra-thoracic fluid status trend feature of Medtronic, Inc. While a large variety of different GUI 500 can be utilized in practicing the present invention, a nominal GUI 500 can include, by illustration and without limitation some of the following. The overlay 501' of GUI 500 is dedicated to a single type of monitored physiologic parameter (as depicted intra-thoracic impedance reflecting possible fluid accumulation within a portion of the heart, lungs and/or pulmonary bed). A baseline reference value can be manipulated via a user-selectable button 508 as a threshold value 504 on GUI overlay 501' for ease of reference. The urgency of the notification signal(s) can be adjusted via button 502 and the notification signal(s) can be suspended as indicated by programmable and adjustable field 506. Once a suspension period has been programmed an optional text message 510 can be configured to display, for example, the date when the notification will again become active. Of course, a similar function can be achieved with a counter (incremental or decremental) in lieu of or in addition to the depicted example.

In accordance with an aspect of the present invention, methods and apparatus are provided for improving notification signaling following a possibly deleterious excursion in a monitored physiologic parameter of a patient.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:
1. A method of selectively deactivating a notification function in an implantable medical device (IMD), comprising:
monitoring a physiologic parameter of a patient indicative of the patient's intrathoracic fluid status;
determining when the physiologic parameter one of exceeds a threshold and departs from a desired range;
energizing the notification function of the IMD responsive to a determination that the physiologic parameter one of exceeds a threshold and departs from a desired range;
receiving corrective or palliative therapy from a clinician subsequent to the determination that the physiologic parameter one of exceeds a threshold and departs from a desired range; and
deactivating the notification function of the IMD for a preset period of time responsive to receipt of the corrective or palliative therapy.

2. A method according to claim 1, wherein the physiologic parameter comprises one of an intra-thoracic fluid parameter and a blood pressure parameter.

3. A method according to claim 1, wherein the notification function provides one of an audible sound and a tactile sensation to the patient.

4. A method according to claim 1, further comprising displaying the physiologic parameter and an indication of the status of the notification function on an external device programming unit.

5. A method according to claim 1, further comprising:
  continuing to monitor the physiologic parameter of the patient.

6. A method according to claim 1, wherein the notification function includes wirelessly broadcasting a notification to an external receiver.

* * * * *